(12) United States Patent
Sakazaki (10) Patent No.: US 9,313,959 B2
(45) Date of Patent: *Apr. 19, 2016

(54) *CALIBRACHOA* PLANT WITH RADIALLY SYMMETRIC COLORATION (75) Inventor: Ushio Sakazaki, Shiga (JP)

(73) Assignee: PLANT 21 LLC, Bonsall, CA (US)

( * ) Notice: Subject to any disclaimer, the term of this patent is extended or adjusted under 35 U.S.C. 154(b) by 875 days.

This patent is subject to a terminal disclaimer.

(21) Appl. No.: 13/420,359

(22) Filed: Mar. 14, 2012

(65) Prior Publication Data

US 2013/0042369 A1   Feb. 14, 2013

Related U.S. Application Data (63) Continuation-in-part of application No. 13/135,599, filed on Jul. 8, 2011, now Pat. No. Plant 23,232.

(30) Foreign Application Priority Data

Mar. 15, 2011   (CA) .......................................... 117221
Oct. 17, 2011   (QZ) ................................... 2011/2462

(51) Int. Cl.
     *A01H 5/02*   (2006.01)

(52) U.S. Cl.
     CPC ........................................ *A01H 5/02* (2013.01)

(58) Field of Classification Search
     USPC ............................................................ Plt./413
     See application file for complete search history.

(56) References Cited

U.S. PATENT DOCUMENTS

PP23,083  P2 *   9/2012   Pierce ............................ Plt./413
PP23,232  P2 *   11/2012  Sakazaki ........................ Plt./413

OTHER PUBLICATIONS

Kanaya et al 2010, Scientia Horticulturae 123: 488-495.*

* cited by examiner

*Primary Examiner* — David H Kruse
(74) *Attorney, Agent, or Firm* — Hauptman Ham, LLP (57) ABSTRACT

The present invention relates to *Calibrachoa* plants displaying at least one inflorescence with a radially symmetric pattern along the center of the fused petal margins, wherein the pattern extends from the center of the inflorescence and does not fade during the life of the inflorescence.

15 Claims, 5 Drawing Sheets
(5 of 5 Drawing Sheet(s) Filed in Color)

CALIBRACHOA PLANT WITH RADIALLY SYMMETRIC COLORATION

CROSS REFERENCE TO RELATED APPLICATIONS

The present application claims priority to Canadian Plant Breeders' Rights application no. 11-7221, filed Mar. 15, 2011 and Community Plant Variety Office Application No. 2011/2462 filed Oct. 17, 2011, and is a continuation-in-part of U.S. application Ser. No. 13/135,599, filed Jul. 8, 2011. Each prior application in its entirety is incorporated herein by reference.

TECHNICAL FIELD

The present disclosure relates generally to the field of ornamental *Calibrachoa* plants, and provides new, distinct, and stable cultivars of *Calibrachoa* plants having inflorescence with a unique radially symmetric pattern along the center of the fused petal margins. The radially symmetric pattern has not been observed in any wild species of *Calibrachoa*, but was discovered through Applicants' breeding process.

INTRODUCTION

The present disclosure relates generally to the field of ornamental *Calibrachoa* plants. The genus *Calibrachoa* belongs to the Solanaceae (nightshade) family, closely related to *Petunias*. Many published plant taxonomies do not recognize *Calibrachoa* as a separate genus, and instead place it under the genus *Petunia*. *Calibrachoa* species can generally be found in South America, in southern Brazil, Peru, and Chile, in much the same regions as *Petunias* are found. Depending on frost conditions, *Calibrachoa* are considered perennials in areas that experience light frost, and annuals in other areas. While *Calibrachoa* produce seed, the resultant progeny generally display a range of characteristics, and so the plants are vegetatively propagated to ensure reproductions that are true-to-type of the originally selected plant.

SUMMARY

In one aspect there is provided a *Calibrachoa* plant comprising at least one inflorescence with a radially symmetric pattern along the center of the fused petal margins, wherein said pattern extends from the center of the inflorescence and does not fade during the life of the inflorescence. In one embodiment, the radially symmetric pattern is yellow, white, or cream. In another embodiment, the radially symmetric pattern extends from the center of the inflorescence to the edge of the petals. In other embodiments, the radially symmetric pattern extends from the center of the inflorescence to less than halfway towards the edge of the petals, more than halfway towards the edge of the petals, or any distance between the center of the inflorescence and the edge of the petals. In another embodiment, the radially symmetric pattern has a color that is not the same as the petal color. In another embodiment, the *Calibrachoa* plant is produced from 'Cherry Star' seed deposited Dec. 5, 2012 at the American Type Culture Collection (ATCC, located at 10801 University Blvd, Manassas, Virginia), a Budapest Treaty recognized depository, wherein the seeds were accorded ATCC Deposit Accession No. PTA-13363.

In another aspect, there is provided a method for producing a *Calibrachoa* plant comprising at least one inflorescence with a radially symmetric pattern along the center of the fused petal margins, comprising (a) crossing, as the male or female parent, a first *Calibrachoa* plant comprising at least one inflorescence with said radially symmetric pattern, with a second *Calibrachoa* plant that does not comprise an inflorescence with said radially symmetric pattern, and (b) selecting progeny that have said radially symmetric pattern wherein said radially symmetric pattern extends from the center of the inflorescence towards the edge of the petals and does not fade during the life of the inflorescence. In one embodiment, the radially symmetric pattern extends from the center of the inflorescence to the edge of the petals. In another embodiment, the method provides a *Calibrachoa* plant, wherein tissue from said plant can be asexually propagated to produce a *Calibrachoa* plant comprising inflorescence with said radially symmetric pattern.

In another aspect, provided herein is a method for asexually reproducing a *Calibrachoa* plant having at least one inflorescence with a radially symmetric pattern along the center of the fused petal margins, comprising (a) obtaining a tissue cutting from said plant, (b) culturing said tissue cutting under conditions sufficient to produce a plantlet with roots and shoots; and (c) growing said plantlet to produce a plant, wherein said pattern extends from the center of the inflorescence towards the edge of the petals and does not fade during the life of the inflorescence. In one embodiment, the radially symmetric pattern extends from the center of the inflorescence to the edge of the petals.

BRIEF DESCRIPTION OF THE PHOTOGRAPHS

This patent or application file contains at least one drawing executed in color. Copies of this patent or patent application publication with color drawing(s) will be provided by the Office upon request and payment of necessary fee.

DETAILED DESCRIPTION

The present inventors discovered a new *Calibrachoa* plant comprising at least one inflorescence with a radially symmetric pattern along the center of the fused petal margins, wherein said pattern extends from the center of the inflorescence towards the edge of the petals and does not fade during the life of the inflorescence. The radially symmetric pattern manifests in several different colors, such that the pattern is not the same color as petal color and thereby contrasts intensely against petal color.

The petal colors of *Calibrachoa* are determined through the interaction of two layers of color pigment, carotenoid and anthocyanin. The carotenoid color may be yellow and the anthocyanin color may be pink, purple, or blue. The present radially symmetric pattern is a result of a mutation and may be controlled by a single half-dominant gene. Regardless of the genetics, the radially symmetric inflorescence pattern can be reproducibly and predictably introgressed into diverse genetic backgrounds of *Calibrachoa* to create new varieties.

As used herein, a radially symmetric pattern refers to a pigmentation pattern that appears during the bud stage and produces a clearly delineated star along each crease in the petals of each flower. The star pattern extends from the center of the inflorescence towards the edge of the petals. In some embodiments, the pattern extends all of the way to the edge of the petals. In other embodiments, the pattern may extend some distance towards the edge of the petals, but not entirely to the edge. For example, and non-limiting, a radially symmetric pattern may extend less than halfway to the petals edge, more than halfway to the petals edge, or any distance between the center of the inflorescence and the edge of the petals. An exemplary radially symmetric pattern can be seen in FIG. 1.

As discussed above, the radially symmetric pattern can manifest as one of several different colors, including but not limited to yellow, white, or cream. Notably, the radially symmetric pattern is not the same color as petal color. For example, if the pattern is yellow (e.g. RHS 13B), then the petals are not yellow, but could be pink, purple, blue, red, scarlet, orange, black, or other non-yellow color. Similarly, if the pattern is white, then the petals are not white, but could be pink, purple, blue, red, scarlet, orange, black, or other non-white color.

"Plant" includes plant cells, plant protoplasts, plant cells of tissue culture from which *Calibrachoa* plants can be regenerated from plant calli, plant clumps and plant cells that are intact in plants or parts of plants such as pollen, flowers, pistils, anthers, seeds, leaves, stems, and the like.

*Petunias*, a close relative of *Calibrachoa*, do not have a carotenoid layer of pigment and so the potential for variation in *Calibrachoa* coloration is much wider than in *Petunias*.

Figure 3:
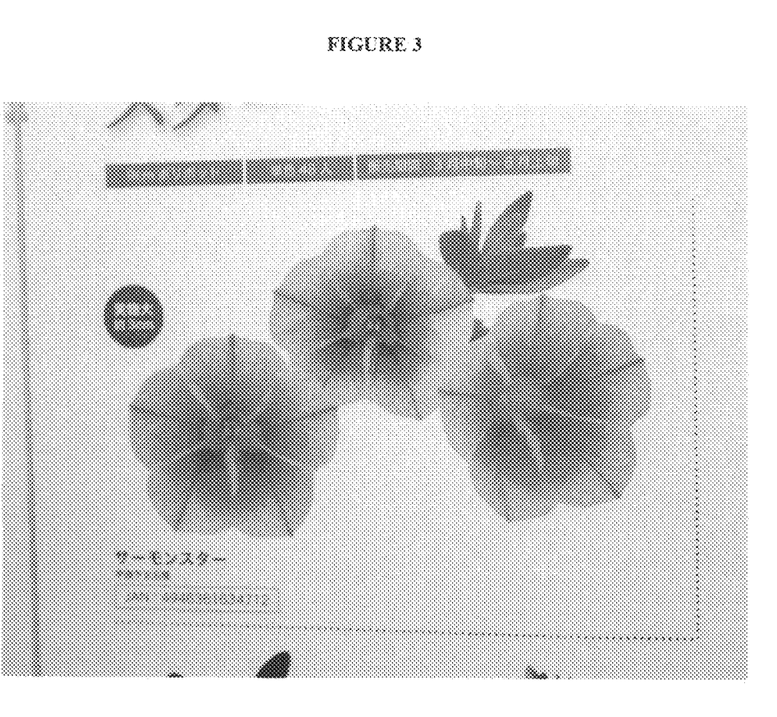
FIG. 3 shows a front view perspective of the prior art example variety 'Salmon Star'.

The instant and novel *Calibrachoa* are most similar to known *Calibrachoa* variety 'Salmon Star', which also exhibits a radially symmetric pattern along the fused petal margins of the inflorescence. However, the coloration in the 'Salmon Star' variety fades over the life of the inflorescence due to differences in the intensity of the anthocyanin layer of coloration. Further, the coloration in 'Salmon Star' is inconsistent, not as pronounced, and does not always extend to the edge of the petals. See, for example, FIG. 3. Whereas 'Salmon Star' has a weaker level of anthocyanin coloration, and thus a weaker presentation of the pattern, the varieties disclosed herein have a stronger contrast between the two layers of coloration, making for a more intense presentation of the pattern, as well as long-lasting coloration that does not fade over time.

A. Breeding History

The radially symmetric inflorescence pattern was first noticed in Spring of 2006 in the seedlings of the *Calibrachoa* variety 'CJ06-13' (breeder reference, unpatented). 'CJ06-13' was developed from a cross between 'C322-2' (breeder reference, unpatented) as the female parent and 'CJ05-52' (breeder reference, unpatented) as the male parent. Neither 'CJ06-13' nor 'CJ05-52' displayed the instant radially symmetric pattern trait.

'CJ06-13' was further crossed with the varieties 'CJ06-02' and 'C413-10' in 2006. Neither 'CJ06-02' nor 'C413-10' displayed the instant pattern trait. The cross between 'CJ06-13' and 'C413-10' produced the variety 'Salmon Star', which displays some evidence of the instant pattern trait as discussed above. In 2007, 'Salmon Star' was crossed as the female parent with the variety 'C508-02' (breeder reference, unpatented) as the male parent to produce the variety 'CJ08-61', a variety with cherry pink flowers and a red pattern. 'C580-02' did not display the instant pattern trait.

Also in 2007, the cross of 'CJ06-13' and 'CJ06-02' which was designated 'C590-08B' (breeder reference, unpatented) and which displayed some evidence of the instant pattern trait, was crossed with the variety 'C403-02' (breeder reference, unpatented) to produce the variety 'CJ08-38', (breeder reference, unpatented), which has a yellow flower color. 'C590-08B' is the product of the cross of 'CJ06-13' and 'CJ06-02'. Neither 'C403-02' nor 'CJ08-38' displayed the instant pattern trait.

In 2008, a cross was made between the variety 'CJ08-61' as the male parent, and 'CJ08-38' as the female parent to produce the instant variety '09C10-01' or 'Cherry Star', which displays the disclosed radially symmetric inflorescence pattern trait with color intensity and longevity over the life of the inflorescence.

B. Stable and Predictable Introgression of the Radially-Symmetric Pattern

The instant radially-symmetric pattern can be stably and predictably introgressed into diverse *Calibrachoa* genetic backgrounds. The instant *Calibrachoa* can be used as a male or female parent in crosses for introducing the trait into new *Calibrachoa* plants, thereby creating diverse *Calibrachoa* genetic backgrounds.

Additionally, and as known in the art, *Calibrachoa* plants can be reproduced asexually by vegetative propagation or other clonal method known in the art. For example, and in no way limiting, a *Calibrachoa* plant having at least one inflorescence with a radially symmetric pattern along the center of the fused petal margins, can be reproduced by (a) obtaining a tissue cutting from said plant, (b) culturing said tissue cutting under conditions sufficient to produce a plantlet with roots and shoots; and (c) growing said plantlet to produce a plant, wherein said pattern extends from the center of the inflorescence towards the edge of the petals and does not fade during the life of the inflorescence.

* * *

The following Examples are illustrative and do not limit the disclosure.

EXAMPLE 1

Botanical Description of '09C10-01' ('Cherry Star')

Botanical Classification:
    *Calibrachoa* sp.
Parentage:
    Female, or seed, parent: Proprietary seedling selection of *Calibrachoa* sp. identified as code name CJ08-5 61, not patented.
    Male, or pollen, parent: Proprietary seedling selection of *Calibrachoa* sp. identified as code number CJ08-38, not patented.
Propagation:
    Type: By terminal cuttings.
    Time to initiate roots, summer: About four days at temperatures ranging from 17° C. to 29° C.
    Time to initiate roots, winter: About six days at temperatures ranging from 17° C. to 21° C.
    Time to produce a rooted plant, summer: About 22 days at temperatures ranging from 17° C. to 29° C.
    Time to produce a rooted plant, winter: About 25 days at temperatures ranging from 17° C. to 21° C.
    Root description: Medium in thickness, fibrous; white in color.
    Rooting habit: Freely branching; medium density.
Plant Description:
    Plant and growth habit: Compact, upright to outwardly spreading and mounding plant habit; freely branching habit 5 with about five primary lateral branches each with about three to four secondary lateral branches; pinching enhances branching; moderately vigorous, dense and bushy growth habit.
  Plant height: About 16 cm.
  Plant diameter: About 30 cm by 37 cm.
Lateral Branch Description:
  Length: About 15 cm.
  Diameter: About 2 mm.
  Internode length, vegetative: About 1 cm.
  Internode length, reproductive: About 1.9 cm.
  Strength: Strong.
  Aspect: Initially upright to outwardly spreading.
  Texture: Pubescent.
  Color: Close to 146C.
Foliage Description:
  Arrangement: Before flowering, alternate; after flowering, opposite; leaves simple.
  Length: About 2.6 cm.
  Width: About 9 mm.
  Shape: Oblanceolate.
  Apex: Rounded.
  Base: Attenuate.
  Margin: Entire.
  Texture, upper and lower surfaces: Pubescent.
  Venation pattern: Pinnate; arcuate.
  Color:
  Developing leaves, upper and lower surfaces: Close to 137B.
  Fully expanded leaves, upper and lower surfaces: Close to 137B; venation, close to 137C.
  Petiole:
  Length: About 4 mm.
  Diameter: About 2 mm.
  Texture, upper and lower surfaces: Pubescent.
  Color, upper surface: Close to 146C.
  Color, lower surface: Close to 146D.
Flower Description:
  Flower arrangement and habit: Single salverform flowers arising from leaf axils; freely flowering habit with usually about 25 to 27 open flowers and flower buds per lateral branch; flowers face upright and outwardly.
  Fragrance: None detected.
  Natural flowering season: Early flowering habit, plants of the new *Calibrachoa* begin flowering about six weeks after planting; plants flower continuously from spring though the autumn in California.
  Flower longevity: Individual flowers last about five days on the plant; flowers persistent.
  Flower diameter: About 3.6 cm.
  Flower length (height): About 2.9 cm.
  Flower throat diameter: About 8 mm by 10 mm.
  Flower tube length: About 2 cm.
  Flower tube diameter, base: About 2.5 mm.
  Flower bud:
  Shape: Elongated oblong.
  Length: About 2.3 cm.
  Diameter: About 6 mm.
  Color: Close to 145D.
  Corolla:
  Arrangement: Five petals fused at the base and opening into a flared trumpet.
  Petal lobe length (from throat): About 1.5 cm.
  Petal lobe width: About 1.7 cm.
  Petal shape: Roughly cordate.
  Petal apex: Emarginate.
  Petal margin: Entire.
  Petal texture, upper surface: Smooth, glabrous; velvety.
  Petal texture, lower surface: Pubescent.
  Throat texture: Smooth, glabrous.
  Tube texture: Pubescent.
  Color:
  Petal lobe, when opening, upper surface: Close to N186D.
  Petal lobe, when opening, lower surface: Close to 198D.
  Petal lobe, fully opened, upper surface: Brighter than 71A; towards the throat, close to 187A; starshaped pattern, close to 13B; primary color becoming closer to 71C with development; venation, close to 71A.
  Petal lobe, fully opened, lower surface: Close to N77B; venation, close to 187B.
  Throat: Close to 12B; venation, 5 close to 145C.
  Tube: Close to 195B; venation, close to 187C.
  Calyx:
  Arrangement: One calyx tube with five sepals in a single whorl and fused at the base.
  Sepal length: About 1.6 cm.
  Sepal width: About 3 mm.
  Sepal shape: Ligulate to narrowly elliptical.
  Sepal apex: Acute.
  Sepal margin: Entire.
  Sepal texture, upper and lower surfaces: Pubescent.
  Color, upper and lower surfaces: Close to 146C.
  Peduncles:
  Length: About 1.5 cm.
  Diameter: About 1 mm.
  Angle: About 30° to 45° from stem axis.
  Strength: Strong.
  Texture: Pubescent.
  Color: Close to 146D.
  Reproductive organs:
  Stamens:
  Quantity: About five per flower.
  Filament length: About 7 mm.
  Filament color: Close to 145D.
  Anther shape: Oval.
  Anther length: About 1 mm.
  Anther color: Close to 5D.
  Pollen amount: Scarce.
  Pollen color: Close to 6B.
  Pistils:
  Quantity: One per flower.
  Pistil length: About 1.2 cm.
  Style length: About 8 mm.
  Style color: Close to 145D.
  Stigma shape: Oval.
  Stigma color: Close to 144A.
  Ovary color: Close to 145C.
  Seeds and fruits:
  Seed and fruit development have not been observed on plants of the new *Calibrachoa*.
Garden Performance:
  Plants of the new *Calibrachoa* have been observed to have good garden performance and tolerate wind, rain and temperatures ranging from about 1° C. to about 40° C.
Pathogen/Pest Resistance:
  Plants of the new *Calibrachoa* have not been observed to be resistant to pathogens and pests common to *Calibrachoa*.

EXAMPLE 2

Comparison of 'Cherry Star' with 'Salmon Star'

The closest known variety to 'Cherry Star' is 'Salmon Star,' which exhibits a modified and transient radially-symmetric pattern. Several features distinguish 'Cherry Star' from 'Salmon Star.'

Figure 1:
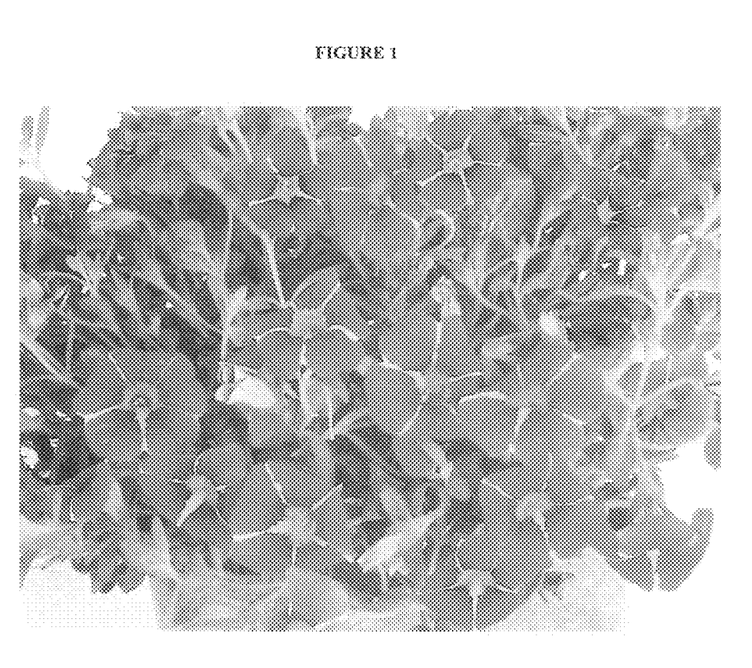
FIG. 1 shows a close-up view of typical inflorescences of 'Cherry Star'.

Foremost, 'Cherry Star' shows an intense contrast between the coloration of the petals and the radially-symmetric coloration pattern. For example, and as shown in FIG. 1, the radially symmetric pattern color contrasts with petal color. Importantly, the radially-symmetric coloration pattern does not fade over time, it persists from the time of the appearance of the flower buds through the flower's life span. Additionally, in 'Cherry Star,' the radially-symmetric coloration pattern consistently extends along the fused petal margins towards the edges of the petals.

Figure 2:
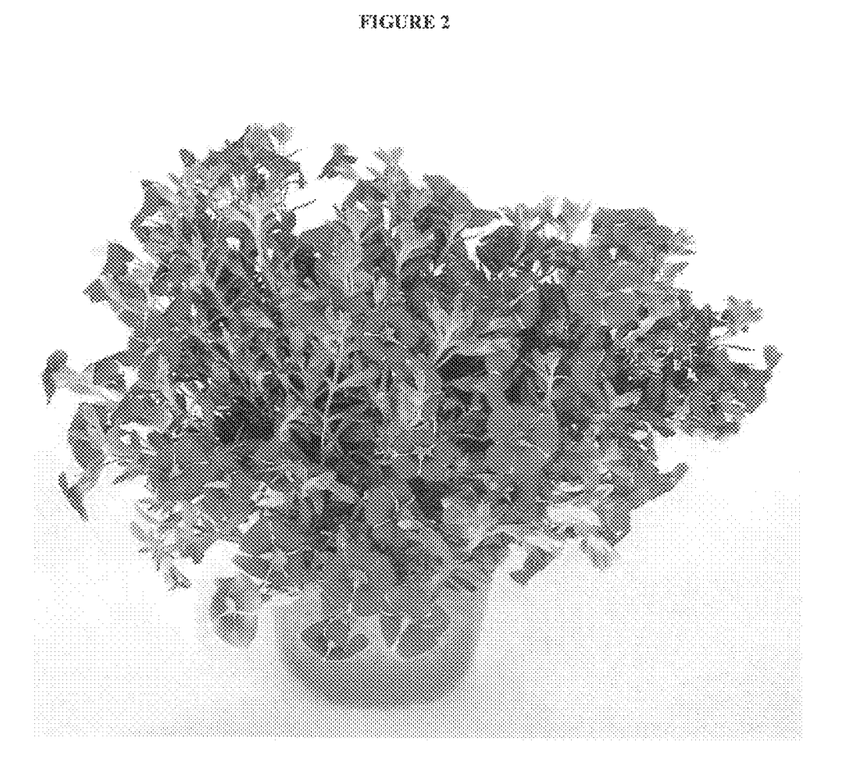
FIG. 2 shows a side perspective view of a typical flowering plant of 'Cherry Star'.

In contrast, 'Salmon Star' does not display as an intense difference between the coloration of the pattern and the coloration of the petals in general. Additionally, and as discussed above and shown in FIG. 1 and FIG. 2, in 'Cherry Star,' the radially-symmetric coloration pattern can extend all of the way along the fused petal margins to the edges of the petals, whereas in 'Salmon Star' (FIG. 3) the coloration pattern does not consistently extend the same length along the fused petal margins or consistently extend to the petal edges.

The below list provides some further characteristics of variety 'Salmon Star'.
Botanical Classification:
  *Calibrachoa* sp. 'USCAL59601'.
Parentage:
  Female, or seed, parent: Proprietary seedling selection of *Calibrachoa* sp. identified as code name C413-10, not patented.
  Male, or pollen, parent: Proprietary seedling selection of *Calibrachoa* sp. identified as code number CJ0613, not patented.
Propagation:
  In vitro vegetative cuttings.
Stable and Predictable Introgression of the Radially-Symmetric Pattern The instant radially-symmetric pattern can be stably and predictably introgressed into diverse *Calibrachoa* genetic backgrounds. The instant *Calibrachoa* can be used as a male or female parent in crosses for introducing the trait into new *Calibrachoa* plants. The discussion below provides examples of the introgression of the instant trait into diverse *Calibrachoa* genetic backgrounds.

EXAMPLE 3

Developing 'Grape Punch Star'

The *Calibrachoa* variety 'Cherry Star' exhibits cherry red colored petals with the claimed radially-symmetric coloration pattern shown in yellow. A similar *Calibrachoa* variety 'Grape Punch' exhibits large grape-purple colored petals with a deep velvet ring and yellow eye. 'Grape Punch' does not exhibit the instant radially-symmetric coloration pattern.

The variety 'Cherry Star' can be crossed as a male parent with the variety 'Grape Punch' as a female parent to produce the progeny 'Grape Punch Star', of which 5-10% of the progeny exhibit the claimed trait. The resulting progeny 'Grape Punch Star' exhibits a large dark blue flower, deep velvet ring, and a stable presentation of the instant radially-symmetric coloration pattern in yellow.

| Male Parent Superbells 'Cherry Star' | Female Parent Superbells 'Grape Punch' | Progeny 'Grape Punch Star' |
|---|---|---|
| Mounding Habit | Mounding Habit | Mounding Habit |
| Flower color cherry red with stable "yellow star" that radiates across petals | Large Grape Flower with deep velvet ring around a yellow eye | Large dark blue flower with deep velvet ring and stable "yellow star" that radiate across petals |

EXAMPLE 4

Developing 'Pomegranate Punch Star'

The *Calibrachoa* variety 'Cherry Star' exhibits cherry red colored petals with the instant radially-symmetric coloration pattern shown in yellow. A similar *Calibrachoa* variety 'Pomegranate Punch' exhibits large red colored petals with a deep velvet red ring and yellow eye. 'Pomegranate Punch' does not exhibit the instant radially-symmetric coloration pattern.

Figure 4:
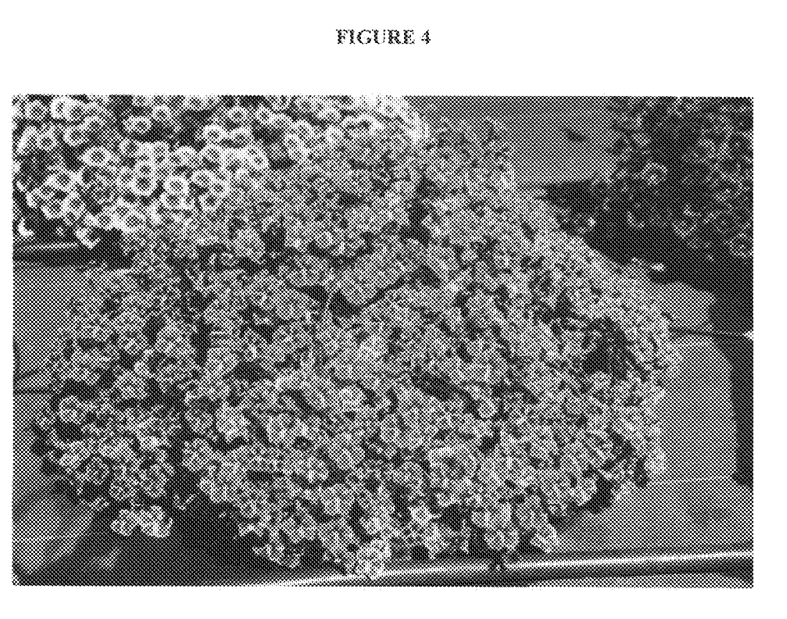
FIG. 4 shows a side perspective view of a typical flowering plant of the progeny variety 'Scarlet Punch Star'.

The variety 'Cherry Star' can be crossed as a male parent with the variety 'Pomegranate Punch' as a female parent to produce the progeny 'Scarlet Punch Star', of which 5-10% of the progeny exhibit the instant trait. The resulting progeny 'Scarlet Punch Star' exhibits a large scarlet flower, deep velvet ring, and a stable presentation of the instant radially-symmetric coloration pattern in yellow. A photograph of the progeny example 'Scarlet Punch Star' is presented as FIG. 4.

| Male Parent Superbells 'Cherry Star' | Female Parent Superbells 'Pomegranate Punch' | Progeny 'Scarlet Punch Star' |
|---|---|---|
| Flower color cherry red with stable "yellow star" that radiates across petals | Large red flower with deep velvet-red ring around a yellow eye | Large scarlet flower with deep velvet ring and stable "yellow star" that radiate across petals |
| Mounding habit | Mounding habit | Mounding habit |

EXAMPLE 5

Developing 'Blackberry Punch Star'

The *Calibrachoa* variety 'Cherry Star' exhibits cherry red colored petals with the instant radially-symmetric coloration pattern shown in yellow. A similar *Calibrachoa* variety 'Blackberry Punch' exhibits purple-pink colored petals with a deep velvet black ring and yellow eye. 'Blackberry Punch' does not exhibit the instant radially-symmetric coloration pattern.

Figure 5:
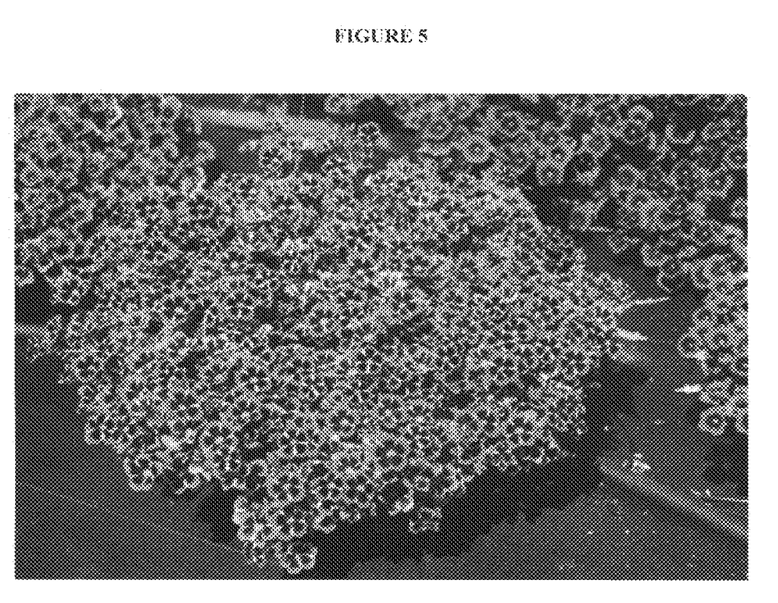
FIG. 5 shows a side perspective view of a typical flowering plant of the progeny variety 'Blackberry Punch Star'.

The variety 'Cherry Star' can be crossed as a male parent with the variety 'Pomegranate Punch' as a female parent to produce the progeny 'Blackberry Punch Star', of which 5-10% of the progeny exhibit the instant trait. The resulting progeny 'Blackberry Punch Star' exhibits a purple-pink flower, deep velvet black ring, and a stable presentation of the instant radially-symmetric coloration pattern in yellow. A photograph of the progeny example 'Blackberry Punch Star' is presented as FIG. 5.

| Male Parent Superbells 'Cherry Star' | Female Parent Superbells 'Blackberry punch' | Progeny 'Blackberry Punch Star' |
|---|---|---|
| Mounding habit Flower color cherry red with stable "yellow star" that radiates across petals | Mounding habit Purple pink flower with deep velvet black ring around a yellow eye | Mounding habit Purple pink flower with deep velvet black ring and stable "yellow star" that radiate across petals |

What is claimed is:

1. A *Calibrachoa* plant comprising at least one inflorescence with a radially symmetric pattern along the center of the fused petal margins, wherein said pattern extends from the center of the inflorescence and does not fade during the life of the inflorescence,
   and wherein the *Calibrachoa* plant comprises a single half-dominant gene, as found in Calibrachoa variety 'Cherry Star,' representative seed having been deposited under ATCC Accession No. PTA-13363.

2. The *Calibrachoa* plant of claim 1, wherein said radially symmetric pattern is yellow, white, cream, or combinations thereof.

3. The *Calibrachoa* plant of claim 1, wherein said radially symmetric pattern extends from the center of the inflorescence to the edge of the petals.

4. The *Calibrachoa* plant of claim 1, wherein said radially symmetric pattern extends from the center of the inflorescence to more than halfway towards the edge of the petals.

5. The *Calibrachoa* plant of claim 1, wherein said radially symmetric pattern extends from the center of the inflorescence to less than halfway towards the edge of the petals.

6. The *Calibrachoa* plant of claim 1, wherein said radially symmetric pattern extends any distance between the center of the inflorescence and the edge of the petals.

7. The *Calibrachoa* plant of claim 1, wherein said radially symmetric pattern has a color that is not the same as the petal color.

8. A *Calibrachoa* plant of claim 1, wherein the plant is produced from seeds having ATCC Deposit Accession No. PTA-13363, which is the variety 'Cherry Star'.

9. A method for producing a *Calibrachoa* plant comprising at least one inflorescence with a radially symmetric pattern along the center of the fused petal margins, comprising
   (a) crossing, as the male or female parent, the *Calibrachoa* plant of claim 1 comprising at least one inflorescence with said radially symmetric pattern, with a *Calibrachoa* plant that does not comprise an inflorescence with said radially symmetric pattern, and
   (b) selecting progeny that have said radially symmetric pattern wherein said radially symmetric pattern extends from the center of the inflorescence towards the edge of the petals and does not fade during the life of the inflorescence.

10. The method of claim 9, wherein said radially symmetric pattern extends from the center of the inflorescence to the edge of the petals.

11. A *Calibrachoa* plant produced by the method of claim 9, wherein tissue from said plant can be asexually propagated to produce a *Calibrachoa* plant comprising inflorescence with said radially symmetric pattern.

12. A method for asexually reproducing a *Calibrachoa* plant having at least one inflorescence with a radially symmetric pattern along the center of the fused petal margins, comprising
    (a) obtaining a tissue cutting from the *Calibrachoa* plant of claim 1,
    (b) culturing said tissue cutting under conditions sufficient to produce a plantlet with roots and shoots; and
    (c) growing said plantlet to produce a plant, wherein said pattern extends from the center of the inflorescence towards the edge of the petals and does not fade during the life of the inflorescence.

13. The method of claim 12, wherein said radially symmetric pattern extends from the center of the inflorescence to the edge of the petals.

14. A method for sexually reproducing a *Calibrachoa* plant comprising at least one inflorescence with a radially symmetric pattern along the center of the fused petal margins, comprising
    (a) selfing the *Calibrachoa* plant of claim 1 comprising at least one inflorescence with said radially symmetric pattern; and
    (b) selecting progeny that have said radially symmetric pattern wherein said radially symmetric pattern extends from the center of the inflorescence towards the edge of the petals and does not fade during the life of the inflorescence.

15. A method for sexually reproducing a *Calibrachoa* plant comprising at least one inflorescence with a radially symmetric pattern along the center of the fused petal margins, comprising
    (a) crossing, as the male or female parent, the *Calibrachoa* plant of claim 1 comprising at least one inflorescence with said radially symmetric pattern, with a *Calibrachoa* plant comprising an inflorescence with said radially symmetric pattern; and
    (b) selecting progeny that have said radially symmetric pattern wherein said radially symmetric pattern extends from the center of the inflorescence towards the edge of the petals and does not fade during the life of the inflorescence.

* * * * *